US008314099B2

(12) United States Patent
Guglielmotti et al.

(10) Patent No.: US 8,314,099 B2
(45) Date of Patent: Nov. 20, 2012

(54) 1-BENZYL-3-HYDROXYMETHYLINDAZOLE DERIVATIVES AND USE THEREOF IN THE TREATMENT OF DISEASES BASED ON THE EXPRESSION OF MCP-1 AND CX3CR1

(75) Inventors: Angelo Guglielmotti, Rome (IT); Guido Furlotti, Rome (IT); Giorgina Mangano, Rome (IT); Nicola Cazzolla, Albano Laziale (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 12/866,814

(22) PCT Filed: Mar. 6, 2009

(86) PCT No.: PCT/EP2009/052660
§ 371 (c)(1),
(2), (4) Date: Aug. 9, 2010

(87) PCT Pub. No.: WO2009/109654
PCT Pub. Date: Sep. 11, 2009

(65) Prior Publication Data
US 2010/0317618 A1 Dec. 16, 2010

(30) Foreign Application Priority Data

Mar. 7, 2008 (EP) .................................. 08425141

(51) Int. Cl.
*A61K 31/5377* (2006.01)
*A61K 31/4439* (2006.01)
*A61K 31/416* (2006.01)
*C07D 413/02* (2006.01)
*C07D 231/56* (2006.01)
*C07D 401/02* (2006.01)

(52) U.S. Cl. ..................... 514/234.5; 514/338; 514/406; 544/140; 546/275.7; 548/361.1

(58) Field of Classification Search ............... 514/234.5, 514/338, 406; 544/140; 546/275.7; 548/361.1
See application file for complete search history.

(56) References Cited

U.S. PATENT DOCUMENTS

| 2006/0047126 A1 | 3/2006 | Georg et al. |
| 2007/0043057 A1 | 2/2007 | Matteucci et al. |

FOREIGN PATENT DOCUMENTS

| EP | 0 382 276 B1 | 8/1995 |
| EP | 0 510 748 B1 | 3/1996 |
| EP | 1 005 332 B1 | 10/2003 |
| EP | 1 675 862 | 7/2006 |
| EP | 1 869 055 | 12/2007 |
| EP | 1 869 056 | 12/2007 |
| WO | WO 99/04770 A2 | 2/1999 |
| WO | WO 2005/033115 A1 | 4/2005 |
| WO | WO 2006/107257 A1 | 10/2006 |
| WO | WO 2006/107258 A1 | 10/2006 |

OTHER PUBLICATIONS

STN, CAplus registry numbers: RN 1070415-98-3, RN 1070416-00-0, RN 1070416-02-2, RN 1070416-04-4, RN 1070416-06-6, RN 1070416-08-8, RN 1070416-14-6, RN 1070416-16-8, RN 1070416-18-0, and RN 1070416-29-3, Accessed Feb. 6, 2012.*
U.S. Appl. No. 12/864,767, filed Jul. 27, 2010, Guglielmotti, et al.
U.S. Appl. No. 12/865,923, filed Aug. 3, 2010, Guglielmotti, et al.
U.S. Appl. No. 12/865,792, filed Aug. 2, 2010, Guglielmotti, et al.
Barrett J. Rollins, "Chemokines", Blood, vol. 90, No. 3, Aug. 1, 1997, 23 Pages.
Marco Baggiolini, "Chemokines and Leukocyte Traffic", Nature, vol. 392, Apr. 9, 1998, pp. 565-568.
Craig Gerard, et al., "Chemokines and Disease", Nature Immunology, vol. 2, No. 2, Feb. 2001, pp. 108-115.
Surendran Mahalingam, et al., "Chemokines and Viruses: Friends or Foes?", Trends in Microbiology, vol. 11, No. 8, Aug. 2003, pp. 383-391.
Nestor E. Rulli, et al., "Ross River Virus: molecular and Cellular Aspects of Disease Pathogenesis", Pharmacology and Therapeutics, vol. 107, 2005, pp. 329-342.
Toshihiro Nanki, et al., "Migration of CX3CR1-Positive T Cells Producing Type 1 Cytokines and Cytotoxic Molecules into the Synovium of Patients with Rheumatoid Arthritis", Arthritis and Rheumatism, vol. 46, No. 11, Nov. 2002, pp. 2878-2883.
Stephan Segerer, et al., "Expression of the Fractalkine Receptor (CX3CR1) in Human Kidney Diseases", Kidney International, vol. 62, 2002, pp. 488-495.
Miguel Sans, et al., "Enhanced Recruitment of CX3CR1+ T Cells by Mucosal Endothelial Cell-Derived Fractalkine in Inflammatory Bowel Disease", Gastroenterology, vol. 132, No. 1, 2007, pp. 139-153.
Ping Liu, et al., "Cross Talk Among Smad, MAPK, and Integrin Signaling Pathways Enhances Adventitial Fibroblast Functions Activated by Transforming Growth Factor $^2$1 and Inhibited by Gax", Arteriosclerosis, Thrombosis, and Vascular Biology, vol. 28, Jan. 10, 2008, 23 Pages.
David H. McDermott, et al., "Chemokine Receptor Mutant CX3CR1-M280 has Impaired Adhesive Function and Correlates with Protection from Cardiovascular Disease in Humans", The Journal of Clinical Investigation, vol. 111, No. 8, Apr. 2003, pp. 1241-1250.

(Continued)

*Primary Examiner* — Joseph K. McKane
*Assistant Examiner* — Samantha Shterengarts
(74) *Attorney, Agent, or Firm* — Oblon, Spivak, McClelland, Maier & Neustadt, L.L.P.

(57) ABSTRACT

The present invention relates to novel 1-benzyl-3-hydroxymethylindazole derivatives according to formula (I) described in the claims, and to a pharmaceutical composition comprising them, together with a pharmaceutically acceptable vehicle. In addition, the present invention relates to the use of novel 1-benzyl-3-hydroxymethylindazole derivatives for the preparation of a pharmaceutical composition that is active in the treatment of diseases based on the expression of MCP-1 and CX3CR1, and to their use in a method for treating or preventing diseases based on the expression of MCP-1 and CX3CR1.

24 Claims, No Drawings

OTHER PUBLICATIONS

Alexander Niessner, et al., "Wound Healing and Inflammation/Infection: Fractalkine Receptor Polymorphisms V249I and T280M as Genetic Risk Factors for Restenosis", Thrombosis and Haemostasis, vol. 94, 2005, pp. 1251-1256.

Marina Sironi, et al., "A Small Synthetic Molecule Capable of Preferentially Inhibiting the Production of the CC Chemokine Monocyte Chemotactic Protein-1", European Cytokine Network, vol. 10, No. 3, Sep. 1999, pp. 437-441.

International Search Report issued Jan. 27, 2010, in PCT/EP2009/052660.

U.S. Appl. No. 13/041,557, Mar. 7, 2011, Guglielmotti, et al.
U.S. Appl. No. 13/497,175, May 2, 2012, Guglielmotti, et al.

* cited by examiner

1-BENZYL-3-HYDROXYMETHYLINDAZOLE DERIVATIVES AND USE THEREOF IN THE TREATMENT OF DISEASES BASED ON THE EXPRESSION OF MCP-1 AND CX3CR1

CROSS REFERENCES TO RELATED APPLICATIONS

This application is a 371 of International Patent Application No. PCT/EP2009/052660, filed on Mar. 6, 2009, and claims priority to European Patent Application No. 08425141.2, filed on Mar. 7, 2008.

FIELD OF THE INVENTION

The present invention relates to 1-benzyl-3-hydroxymethylindazole derivatives, to a pharmaceutical composition comprising them, and to their use in the treatment of diseases based on the expression of MCP-1 and CX3CR1.

In particular, the present invention relates to novel 1-benzyl-3-hydroxymethylindazole derivatives according to formula (I) below, and to a pharmaceutical composition comprising them together with a pharmaceutically acceptable vehicle. In addition, the present invention relates to the use of novel 1-benzyl-3-hydroxymethylindazole derivatives for preparing a pharmaceutical composition that is active in the treatment of diseases based on the expression of MCP-1 and CX3CR1, and to their use in a method for treating or preventing diseases based on the expression of MCP-1 and CX3CR1.

BACKGROUND OF THE ART

As is known, MCP-1 (Monocyte Chemotactic Protein-1) is a protein belonging to the β subfamily of chemokines. MCP-1 has powerful chemotactic action on monocytes and exerts its action also on T lymphocytes, mastocytes and basophils (Rollins B. J., Chemokines, Blood 1997; 90: 909-928; M. Baggiolini, Chemokines and leukocyte traffic, Nature 1998; 392: 565-568).

Other chemokines belonging to the β subfamily are, for example, MCP-2 (Monocyte Chemotactic Protein-2), MCP-3, MCP-4, MIP-1α and MIP-1β, RANTES.

The β subfamily differs from the α subfamily in that, in the structure, the first two cysteines are adjacent for the β subfamily, whereas they are separated by an intervening amino acid for the α subfamily.

MCP-1 is produced by various types of cells (leukocytes, platelets, fibroblasts, endothelial cells and smooth muscle cells).

Among all the known chemokines, MCP-1 shows the highest specificity for monocytes and macrophages, for which it constitutes not only a chemotactic factor but also an activation stimulus, consequently inducing processes for producing numerous inflammatory factors (superoxides, arachidonic acid and derivatives, cytokines/chemokines) and amplifying the phagocytic activity.

The secretion of chemokines in general, and of MCP-1 in particular, is typically induced by various pro-inflammatory factors, for instance interleukin-1 (IL-1), interleukin-2 (IL-2), TNFα (Tumour Necrosis Factor α), interferon-γ and bacterial lipopolysaccharide (LPS).

Prevention of the inflammatory response by blocking the chemokine/chemokine receptor system represents one of the main targets of pharmacological intervention (Gerard C. and Rollins B. J., Chemokines and disease. Nature Immunol. 2001; 2:108-115).

There is much evidence to suggest that MCP-1 plays a key role during inflammatory processes and has been indicated as a new and validated target in various pathologies.

Evidence of a considerable physiopathological contribution of MCP-1 has been obtained in the case of patients with articular and renal inflammatory diseases (rheumatoid arthritis, lupus nephritis, diabetic nephropathy and rejection following transplant).

However, more recently, MCP-1 has been indicated among the factors involved in inflammatory pathologies of the CNS (multiple sclerosis, Alzheimer's disease, HIV-associated dementia) and other pathologies and conditions, with and without an obvious inflammatory component, including atopic dermatitis, colitis, interstitial lung pathologies, restenosis, atherosclerosis, complications following a surgical intervention (for instance angioplasty, arterectomy, transplant, organ and/or tissue replacement, prosthesis implant), cancer (adenomas, carcinomas and metastases) and even metabolic diseases such as insulin resistance and obesity.

In addition, despite the fact that the chemokine system is involved in controlling and overcoming viral infections, recent studies have demonstrated that the response of certain chemokines, and in particular of MCP-1, may have a harmful role in the case of host-pathogen interactions. In particular, MCP-1 has been indicated among the chemokines that contribute towards organ and tissue damage in pathologies mediated by alpha viruses characterized by monocyte/macrophage infiltration in the joints and muscles (Mahalingam S. et al. Chemokines and viruses: friend or foes? Trends in Microbiology 2003; 11: 383-391; Rulli N. et al. Ross River Virus: molecular and cellular aspects of disease pathogenesis. 2005; 107: 329-342).

Monocytes are the main precursors of macrophages and dendritic cells, and play a critical role as mediators of inflammatory processes. CX3CR1, with its ligand CX3CL1 (fractalkine), represents a key factor in regulating the migration and adhesiveness of monocytes. CX3CR1 is expressed in monocytes, whereas CX3CL1 is a transmembrane chemokine in endothelial cells. Genetic studies in man and in animal models have demonstrated an important role in the physiopathology of inflammatory diseases of CX3CR1 and CX3CL1. There is in fact much evidence to suggest a key contribution of CX3CR1 and of its ligand in the pathogenesis and progression of articular, renal, gastrointestinal and vascular inflammatory diseases (e.g. rheumatoid arthritis, lupus nephritis, diabetic nephropathy, Crohn's disease, ulcerative colitis, restenosis and atherosclerosis).

The expression of CX3CR1 is over-regulated in T cells, which are believed to accumulate in the synovium of patients suffering from rheumatoid arthritis. In addition, the expression of CX3CL1 is over-regulated in endothelial cells and fibroblasts present in the synovium of these patients. Consequently, the CX3CR1/CX3CL1 system plays an important role in controlling the type of cell and the mode of infiltration of the synovium and contributes towards the pathogenesis of rheumatoid arthritis (Nanki T. et al., "Migration of CX3CR1-positive T cells producing type 1 cytokines and cytotoxic molecules into the synovium of patients with rheumatoid arthritis", Arthritis & Rheumatism (2002), vol. 46, No. 11, pp. 2878-2883).

In patients suffering form renal damage, the majority of the inflammatory leukocytes that infiltrate the kidneys express CX3CR1, and in particular it is expressed on two of the main cell types involved in the most common inflammatory renal pathologies and in kidney transplant rejection, T cells and monocytes (Segerer S. et al., Expression of the fractalkine receptor (CX3CR1) in human kidney diseases, Kidney International (2002) 62, pp. 488-495).

Participation of the CX3CR1/CX3CL1 system has been suggested also in inflammatory bowel diseases (IBD). In point of fact, in the case of patients suffering from IBD (e.g. Crohn's disease, ulcerative colitis), a significant increase in the production of CX3CL1 by the intestinal capillary system and a significant increase in CX3CR1-positive cells have been demonstrated, both at the circulatory level and in the mucosa (Sans M. et al., "Enhanced recruitment of CX3CR1+T cells by mucosal endothelial cell-derived fractalkine in inflammatory bowel diseases", Gastroenterology 2007, vol. 132, No. 1, pp. 139-153).

Even more interesting is the demonstration of the key role played by the CX3CR1/CX3CL1 system in vascular damage and in particular under pathological conditions, for instance atherosclerosis and restenosis. CX3CR1 is indicated as a critical factor in the process of infiltration and accumulation of monocytes in the vascular wall, and CX3CR1 polymorphism in man is associated with a reduced prevalence of atherosclerosis, coronary disorders and restenosis (Liu P. et al., "Cross-talk among Smad, MAPK and integrin signalling pathways enhances adventitial fibroblast functions activated by transforming growth factor-1 and inhibited by Gax" Arterioscler. Thromb. Vasc. Biol. 2008; McDermott D. H. et al., "Chemokine receptor mutant CX3CR1-M280 has impaired adhesive function and correlates with protection from cardiovascular diseases in humans", J. Clin. Invest. 2003; Niessner A. et al., Thrombosis and Haemostasis 2005).

European patent EP-B-0 382 276 describes a number of 1-benzyl-3-hydroxymethylindazole derivatives endowed with analgesic activity. In turn, European patent EP-B-0 510 748 describes, on the other hand, the use of these derivatives for preparing a pharmaceutical composition that is active in the treatment of autoimmune diseases. Finally, European patent EP-B-1 005 332 describes the use of these derivatives for preparing a pharmaceutical composition that is active in treating diseases derived from the production of MCP-1. 2-Methyl-2-{[1-(phenylmethyl)-1H-indazol-3-yl] methoxy}propanoic acid is thought to be capable of inhibiting, in a dose-dependent manner, the production of MCP-1 and TNF-α induced in vitro in monocytes from LPS and Candida albicans, whereas the same compound showed no effects in the production of cytokines IL-1 and IL-6, and of chemokines IL-8, MIP-1α, and RANTES (Sironi M. et al., "A small synthetic molecule capable of preferentially inhibiting the production of the CC chemokine monocyte chemotactic protein-1", European Cytokine Network. Vol. 10, No. 3, 437-41, September 1999).

European patent applications EP-A-1 869 055, EP-A-1 869 056 and EP-A-1 675 862 describe 1,3-thiazolo-4,5-pyrimidine derivatives that are capable of acting as CX3CR1 receptor antagonists.

Despite the activity developed thus far, there is still felt to be a need for novel pharmaceutical compositions and compounds that are effective in the treatment of diseases based on the expression of MCP-1 and CX3CR1.

The Applicant has found, surprisingly, novel 1-benzyl-3-hydroxymethylindazole derivatives with pharmacological activity.

The Applicant has found, surprisingly, that the novel 1-benzyl-3-hydroxymethylindazole derivatives according to formula (I) of the present invention are capable of reducing the production of the chemokine MCP-1.

More surprisingly, the Applicant has found that the novel 1-benzyl-3-hydroxymethylindazole derivatives according to formula (I) of the present invention are capable of reducing the expression of the chemokine MCP-1.

Even more surprisingly, the Applicant has found that the novel 1-benzyl-3-hydroxymethylindazole derivatives according to formula (I) of the present invention are capable of reducing the expression of the receptor CX3CR1.

Thus, in a first aspect, the present invention consists of a compound of formula (I)

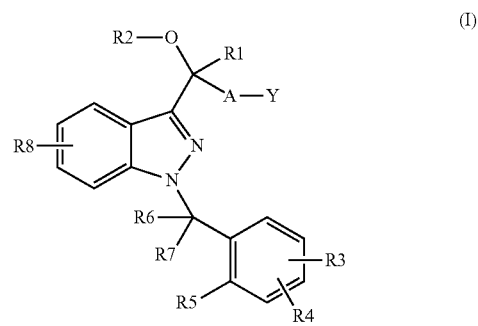

in which:
A may be $-X_1-$ or $-X_1-O-X_2-$, in which
  $X_1$ may be an alkyl group having from 1 to 5 carbon atoms, optionally substituted with one or more alkyl groups having from 1 to 5 carbon atoms, and
  $X_2$ may be an alkyl group having from 1 to 5 carbon atoms, optionally substituted with one or more alkyl groups having from 1 to 5 carbon atoms or one or more alkoxy groups having from 1 to 3 carbon atoms,
Y may be hydrogen, $-OH$, $-N(R_{11})(R_{12})$, $-N(R_{11})O(R_{12})$, in which
  $R_{11}$ may be hydrogen, an alkyl group having from 1 to 5 carbon atoms, an alkoxy group having from 1 to 3 carbon atoms, or $R_{11}$ together with $R_{12}$ forms a 4- to 7-membered heterocycle,
  $R_{12}$ may be hydrogen, an alkyl group having from 1 to 5 carbon atoms, an alkoxy group having from 1 to 3 carbon atoms, an aryl group, a heteroaryl group, an alkylaryl group, an alkylheteroaryl group, COR', COOR', CON(R')(R") with R' and R", which may be identical or different each other, represented by hydrogen and an alkyl group having from 1 to 5 carbon atoms, or $R_{12}$ together with $R_{11}$, forms a 4- to 7-membered heterocycle,
$R_1$ and $R_2$, which may be identical or different each other, may be hydrogen, an alkyl group having from 1 to 5 carbon atoms,
$R_3$, $R_4$ and $R_8$, which may be identical or different each other, may be hydrogen, an alkyl group having from 1 to 5 carbon atoms, an alkoxy group having from 1 to 3 carbon atoms, a halogen atom, $-OH$, $-N(R')(R")$, $-N(R')COR"$, $-CN$, $-CONR'R"$, $-SO_2NR'R"$, $-SO_2R'$, nitro and trifluoromethyl; with R' and R", which may be identical or different each other, represented by hydrogen and an alkyl group having from 1 to 5 carbon atoms,
$R_5$ may be hydrogen, an alkyl group having from 1 to 5 carbon atoms, an alkoxy group having from 1 to 3 carbon atoms, a halogen atom, $-OH$, $-N(R)(R")$, $-N(R')COR"$, nitro and trifluoromethyl, or $R_5$ together with one from between $R_6$ and $R_7$ forms a ring having 5 or 6 carbon atoms; with R' and R", which may be identical or different each other, represented by hydrogen and an alkyl group having from 1 to 5 carbon atoms, $R_6$ and $R_7$, which may be identical or different each other, may be hydrogen, an alkyl group having from 1 to 5 carbon atoms, or together form a group C=O, or one from between $R_6$ and $R_7$, together with $R_5$, forms a ring having 5 or 6 carbon atoms.

In a second aspect, the present invention relates to a pharmaceutical composition comprising the novel 1-benzyl-3-hydroxymethylindazole derivatives according to formula (I) or a pharmaceutically acceptable salt thereof together with at least one pharmaceutically acceptable vehicle.

The over-regulation and/or the increase of the expression of the above mentioned MCP-1, CX3CR1, and p40, the latest resulting consequently in IL-12 and/or IL-23 expression/production, which results in a development of a pathology and/or a disease is often referred in the art with the term "overexpression". For the purpose of the present invention, the term expression is intended to include overexpression as known in the art.

Surprisingly, the Applicant has found that the novel 1-benzyl-3-hydroxymethylindazole derivatives according to formula (I) of the present invention may be used for the preparation of a pharmaceutical composition that is active in the treatment of diseases based on the expression of the chemokine MCP-1 and of the receptor CX3CR1.

Thus, in a third aspect, the present invention relates to the use of a compound of formula (I)

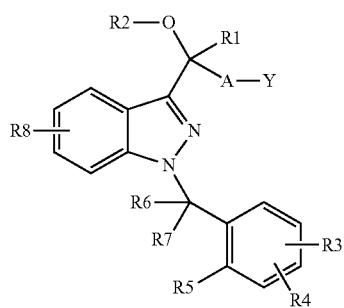

in which:
A may be —$X_1$— or —$X_1$—O—$X_2$—, in which
$X_1$ may be an alkyl group having from 1 to 5 carbon atoms, optionally substituted with one or more alkyl groups having from 1 to 5 carbon atoms, and
$X_2$ may be an alkyl group having from 1 to 5 carbon atoms, optionally substituted with one or more alkyl groups having from 1 to 5 carbon atoms or one or more alkoxy groups having from 1 to 3 carbon atoms,
Y may be hydrogen, —OH, —N($R_{11}$)($R_{12}$), —N($R_{11}$)O($R_{12}$), in which
$R_{11}$ may be hydrogen, an alkyl group having from 1 to 5 carbon atoms, an alkoxy group having from 1 to 3 carbon atoms, or $R_{11}$ together with $R_{12}$ forms a 4- to 7-membered heterocycle,
$R_{12}$ may be hydrogen, an alkyl group having from 1 to 5 carbon atoms, an alkoxy group having from 1 to 3 carbon atoms, an aryl group, a heteroaryl group, an alkylaryl group, an alkylheteroaryl group, COR', COOR', CON(R')(R") with R' and R", which may be identical or different each other, represented by hydrogen and an alkyl group having from 1 to 5 carbon atoms, or $R_{12}$ together with $R_{11}$, forms a 4- to 7-membered heterocycle, $R_1$ and $R_2$, which may be identical or different each other, may be hydrogen, an alkyl group having from 1 to 5 carbon atoms,
$R_3$, $R_4$ and $R_8$, which may be identical or different each other, may be hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —SO$_2$NR'R", —SO$_2$R', nitro and trifluoromethyl; with R' and R", which may be identical or different each other, represented by hydrogen and an alkyl group having from 1 to 5 carbon atoms,
$R_5$ may be hydrogen, an alkyl group having from 1 to 5 carbon atoms, an alkoxy group having from 1 to 3 carbon atoms, a halogen atom, —OH, —N(R)(R"), —N(R')COR", nitro and trifluoromethyl, or $R_5$ together with one from between $R_6$ and $R_7$ forms a ring having 5 or 6 carbon atoms; with R' and R", which may be identical or different each other, represented by hydrogen and an alkyl group having from 1 to 5 carbon atoms,
$R_6$ and $R_7$, which may be identical or different each other, may be hydrogen, an alkyl group having from 1 to 5 carbon atoms, or together form a group C=O, or one from between $R_6$ and $R_7$, together with $R_5$, forms a ring having 5 or 6 carbon atoms,
for preparing a pharmaceutical composition for the treatment of diseases based on the expression of MCP-1 and CX3CR1.

In addition, in a fourth aspect, the present invention relates to a method for treating or preventing diseases based on the expression of MCP-1 and CX3CR1, characterized by the administration to a person in need thereof an effective amount of the compound of formula (I) previously described.

DETAILED DESCRIPTION OF THE INVENTION

In formula (I) previously described, residue A is represented by the group —$X_1$— or by the group —$X_1$—O—$X_2$—.

Preferably, in formula (I) previously described, $X_1$ may be an alkyl group having from 1 to 4 carbon atoms, optionally substituted with one or more alkyl groups having from 1 to 3 carbon atoms, and $X_2$ is an alkyl group having from 1 to 4 carbon atoms, optionally substituted with one or more alkyl groups having from 1 to 3 carbon atoms or one or more alkoxy groups having 1 or 2 carbon atoms.

More preferably, $X_1$ is a group CH$_2$, a group CH$_2$CH$_2$, a group C(CH$_3$)$_2$, or a group C(CH$_3$)$_2$CH$_2$.

More preferably, $X_2$ is a group CH$_2$, a group CH$_2$CH$_2$, a group CH$_2$CH$_2$CH$_2$, a group C(CH$_3$)$_2$, a group C(CH$_3$)$_2$CH$_2$, or a group CH$_2$C(CH$_3$)$_2$CH$_2$.

Advantageously, in formula (I) previously described, residue A is represented by the group $X_1$, and preferably by the group CH$_2$, and by the group C(CH$_3$)$_2$.

Advantageously, in formula (I) previously described, residue A is represented by the group —$X_1$—O—$X_2$—, and preferably by the group CH$_2$OCH$_2$CH$_2$ and by the group CH$_2$OCH$_2$CH$_2$CH$_2$.

In formula (I) previously described, Y may be hydrogen, —OH, —N($R_{11}$)($R_{12}$), —N($R_{11}$)O($R_{12}$).

Advantageously, $R_{11}$ is represented by a hydrogen atom, an alkyl group having from 1 to 3 carbon atoms, or $R_{11}$ together with $R_{12}$ forms a 5- or 6-membered heterocycle.

Advantageously, $R_{12}$ is represented by a hydrogen atom, an alkyl group having from 1 to 3 carbon atoms, or $R_{12}$ together with $R_{11}$ forms a 5- or 6-membered heterocycle.

Preferably, $R_1$ and $R_2$, which may be identical or different each other, are represented by a hydrogen atom, an alkyl group having from 1 to 3 carbon atoms.

Preferably, $R_3$, $R_4$ and $R_8$, which may be identical or different each other, are represented by a hydrogen atom, an alkyl group having from 1 to 3 carbon atoms, an alkoxy group having 1 or 2 carbon atoms, a Br, Cl or F atom, an OH group, a nitro group, a trifluoromethyl group or a group N(R')(R"), —N(R')COR", —CN, —CONR'R", —SO$_2$NR'R", —SO$_2$R', with R' and R", which may be identical or different each other, represented by a hydrogen atom and an alkyl group having from 1 to 3 carbon atoms.

Advantageously, $R_5$ is represented by a hydrogen atom, an alkyl group having from 1 to 3 carbon atoms, an alkoxy group having 1 or 2 carbon atoms, a halogen atom, an OH group, or $R_5$, together with one from between $R_6$ and $R_7$, forms a ring having 5 or 6 carbon atoms.

Preferably, $R_6$ and $R_7$, which may be identical or different each other, are represented by a hydrogen atom, an alkyl group having from 1 to 3 carbon atoms, or together form a group C=O, or one from between $R_6$ and $R_7$, together with $R_5$, forms a ring having 5 or 6 carbon atoms.

In the case of certain substituents, the compound of formula (I) according to the present invention may be an asymmetric carbon atom and may then be in the form of stereoisomers and enantiomers.

Depending on the nature of the substituents, the compound of formula (I) may form addition salts with physiologically acceptable organic or mineral acids or bases.

Typical examples of suitable physiologically acceptable mineral acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

Typical examples of suitable physiologically acceptable mineral bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

Depending on the nature of the substituents, the compound of formula (I) may form esters with physiologically acceptable organic acids. Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

The compounds of the present invention also include the prodrugs, stereoisomers, enantiomers and pharmaceutically acceptable salts or esters of the compounds represented by formula (I) described in the claims. The prodrug of a compound of formula (I) is a substance in substantially inactive form, which, when administered to a living being, is metabolized into a compound of formula (I).

The terms "pharmaceutically acceptable" and "physiologically acceptable" are intended to define, without any particular limitation, any material suitable for preparing a pharmaceutical composition to be administered to a living being.

The compounds according to formula (I) of the present invention may be used for the preparation of a pharmaceutical composition that is active in the treatment of diseases (or pathologies) based on the expression of the chemokine MCP-1 and the receptor CX3CR1.

Preferably, the pathologies associated with the expression of MCP-1 and CX3CR1 are articular diseases, renal diseases, cardiovascular diseases, metabolic syndrome, obesity, diabetes, insulin resistance and cancer.

In particular, the pathologies associated with the expression of MCP-1 are rheumatoid arthritis, arthritis induced by viral infections, psoriatic arthritis, arthrosis, lupus nephritis, diabetic nephropathy, glomerulonephritis, polycystic kidney disease, interstitial lung disease, fibrosis, multiple sclerosis, Alzheimer's disease, HIV-associated dementia, atopic dermatitis, psoriasis, vasculitis, restenosis, atherosclerosis, myocardial infarction, angina, acute coronary diseases, adenomas, carcinomas and metastases, metabolic diseases and complications following surgical interventions such as, for example, angioplasty, arterectomy, circulation recovery techniques, transplants, organ replacements, tissue replacements and prosthesis implants.

In particular, the pathologies associated with the expression of CX3CR1 are rheumatoid arthritis, lupus nephritis, diabetic nephropathy, Crohn's disease, ulcerative colitis, coronary disorders, restenosis, atherosclerosis, myocardial infarction, angina, and complications following surgical interventions such as, for example, angioplasty, arterectomy and circulation recovery techniques.

Preferably, the pharmaceutical compositions of the present invention are prepared in suitable dosage forms comprising an effective dose of at least one compound of formula (I), or a pharmaceutically acceptable salt, ester or prodrug thereof, and at least one pharmaceutically acceptable vehicle.

Examples of pharmaceutically acceptable vehicles known in the prior art are, for example, glidants, binders, disintegrants, fillers, diluents, flavourings, colorants, fluidizers, lubricants, preserving agents, humectants, absorbents and sweeteners.

Useful examples of pharmaceutically acceptable excipients are sugars, such as lactose, glucose or sucrose, starches, such as corn starch and potato starch, cellulose and derivatives thereof, for instance sodium carboxymethylcellulose, ethylcellulose and cellulose acetate, gum tragacanth, malt, gelatin, talc, cocoa butter, waxes, oils, such as groundnut oil, cottonseed oil, safflower oil, sesame oil, olive oil, corn oil and soybean oil, glycols such as propylene glycol, polyols such as glycerol, sorbitol, mannitol and polyethylene glycol, esters such as ethyl oleate and ethyl laurate, agar-agar, and the like.

Examples of suitable dosage forms are tablets, capsules, coated tablets, granules, solutions and syrups for oral administration; medicated plasters, solutions, pastes, creams and ointments for transdermal administration; suppositories for rectal administration and sterile solutions for injection or aerosol administration.

Other suitable dosage forms are sustained-release forms and liposome-based forms, for either the oral or injection route.

The dosage forms may also contain other conventional ingredients such as: preserving agents, stabilizers, surfactants, buffers, osmotic pressure regulators, emulsifiers, sweeteners, colorants, flavourings and the like.

When required for particular therapies, the pharmaceutical composition of the present invention may contain other pharmacologically active ingredients whose simultaneous administration is useful.

The amount of compound of formula (I) or of pharmaceutically acceptable salt, ester or prodrug thereof in the pharmaceutical composition of the present invention may vary within a wide range as a function of known factors, for instance the type of pathology to be treated, the severity of the disease, the body weight of the patient, the dosage form, the chosen route of administration, the number of daily administrations and the efficacy of the chosen compound of formula (I). However, the optimum amount may be determined simply and routinely by a person skilled in the art.

Typically, the amount of compound of formula (I) or of pharmaceutically acceptable salt, ester or prodrug thereof in the pharmaceutical composition of the present invention will be such that it ensures a level of administration of between 0.001 and 100 mg/kg/day. Preferably, the level of administration is between 0.05 and 50 mg/kg/day and even more preferably between 0.1 and 10 mg/kg/day.

The dosage forms of the pharmaceutical composition of the present invention may be prepared according to techniques that are well known to pharmaceutical chemists, including mixing, granulation, compression, dissolution, sterilization and the like.

The activity of the compounds of the present invention on MCP-1 and CX3CR1 was demonstrated in vitro in human monocytes via techniques of gene expression analysis with "real-time" RT-PCR and by protein production analysis via an immunoenzymatic test. As is known to those skilled in the art, the abovementioned experimental models are considered useful for checking the activity of the compounds with regard to the expression and production of MCP-1 and the expression of CX3CR1. Consequently, the above-mentioned models may be considered as predictive of the activity in man for the treatment of pathologies characterized by the expression and production of MCP-1, by the expression of CX3CR1 and by inflammatory conditions with the presence of infiltrates rich in monocytes and macrophages.

The preparation of the compounds of general formula (I) may be performed according to one of the following procedures.

Method (A):

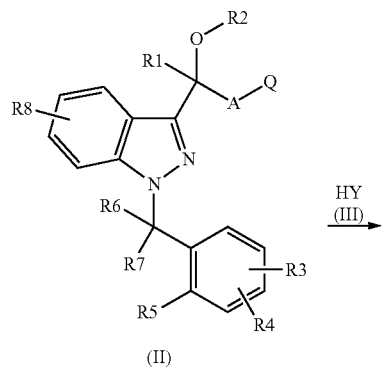

(II)

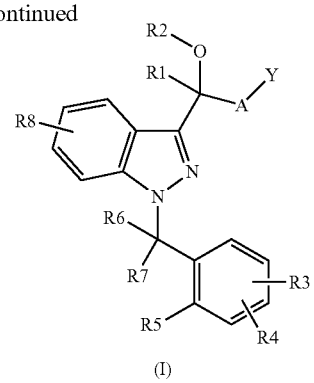

(I)

In method (A), the products of general formula (III), in which Q indicates a leaving group chosen from the group comprising halogen, $CH_3SO_3$— and $p$-$CH_3PhSO_3$—, are reacted with the alcohols and amines of general formula (III). The substituents $R_1$ to $R_8$, A and Y have the meanings given previously for the compounds of formula (I).

Method (A) may be performed according to conventional techniques.

For example, the amines of general formula (III) are reacted with the derivatives of formula (II) in the presence of a suitable base and in a suitable solvent. Preferably, Q is a leaving group preferably chosen from the group comprising a chlorine atom, a bromine atom and a methanesulfonyl group. The bases preferably used are sodium carbonate, potassium carbonate, and aliphatic amines such as triethylamine, diisopropylethylamine or the same reactive amine (III). The solvents that are preferably used are generally polar aprotic solvents such as N,N-dimethylformamine, tetrahydrofuran and dichloromethane. In general, the reaction is performed at a temperature between room temperature and the reflux temperature of the solvent used. Reactions of this type may last from a few hours to a few days.

When the compounds of formula (III) are alcohols, the conventional reaction techniques may use a suitable strong base such as NaH, butyl lithium and lithium diisopropylamide, and suitable polar aprotic solvents such as tetrahydrofuran, diethyl ether or 1,4-dioxane. The temperature at which this type of reaction is generally carried out varies between room temperature and the reflux temperature of the solvent used. Reactions of this type may last from a few hours to a few days.

Method (B):

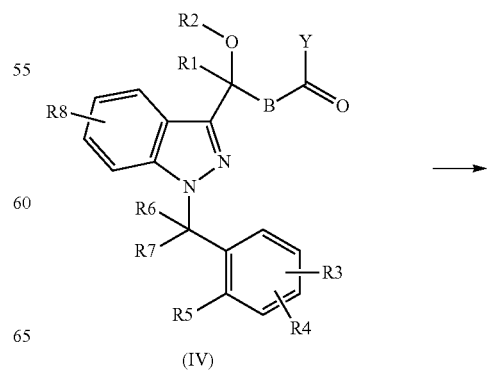

(IV)

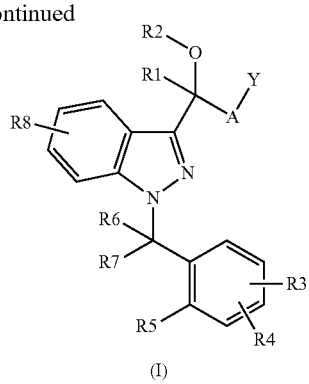

(I)

In which the carboxylic derivatives of general formula (IV) are reduced to the products of general formula (I). The substituents $R_1$ to $R_8$, A and Y have the meanings given previously for the compounds of formula (I), and in which the group B—$CH_2$ has the same meaning as A.

Method (B) may be performed according to conventional methods.

For example, the reduction of the carboxylic compounds of formula (IV) may be carried out with the aid of reducing reagents such as lithium aluminium hydride, sodium borohydride or organometallic agents such as Grignard reagents. In general, the reaction is carried out in a suitable aprotic solvent such as, for example, tetrahydrofuran, diethyl ether and 1,4-dioxane.

The reactions are generally carried out at a temperature that may vary from around 0° C. to the reflux temperature of the solvent, while they may last from 1-2 hours to 24 hours.

The examples that follow are intended to illustrate the present invention without, however, limiting it in any way.

PREPARATIVE EXAMPLES

The compounds of formula (I) listed in Table A below were prepared using the preparation methods previously described.

The details of the preparation of compounds 1 and 2 are given hereinbelow. Compounds 3 to 23 were prepared with similar techniques using suitable starting products and reagents.

Preparation of Compound 1

2-amino-1-(1-benzyl-1H-indazol-3-yl)ethanol 1a) 1-(1-benzylindazol-3-yl)-2-nitroethanol To a suspension of 1-benzyl-3-formylindazole (18 g; 0.076 mol) in anhydrous ethanol (100 ml) stirred at about 5° C. were added nitromethane (9.4 g; 0.154 mol) and, slowly, a solution of sodium (3.5 g; 0.152 mol) in methanol (42 ml). Once the additions were complete, the mixture was stirred at this same temperature of about 5° C. for 3 hours, and the reaction was then completed by filtering off the solid thus formed. The solid was suspended in diethyl ether (100 ml) and stirred at 0° C. A solution of glacial acetic acid (18 g; 0.30 mol) in cold anhydrous diethyl ether (250 ml) was then added to the mixture. Once the additions were complete, the mixture was stirred under cold conditions for 2 hours and then warmed to room temperature and left at this temperature overnight.

The reaction was completed by adding water and ice (500 ml) and separating out the organic phase. This organic phase was washed first with cold 5% $Na_2CO_3$ solution (5×100 ml) and then with cold water until neutral (3×50 ml). The organic phase was then concentrated under reduced pressure and the crude residue obtained was purified by crystallization from hexane and then from benzene.

20 g of 1-(1-benzylindazol-3-yl)-2-nitroethanol were thus obtained.

m.p.=100-101° C.

Elemental analysis: C (64.41%), H (5.40%), N (14.31%).

1b) 2-amino-1-(1-benzyl-1H-indazol-3-yl)ethanol

A mixture of 1-(1-benzylindazol-3-yl)-2-nitroethanol (22 g; 0.074 mol) and Raney nickel (12 ml) in absolute ethanol (200 ml) was placed under a hydrogen atmosphere in a model

TABLE A

| | | | Groups R | | | | | | | |
|---|---|---|---|---|---|---|---|---|---|---|
| No. | A | Y | 1 | 2 | 3 | 4 | 5 | 6 | 7 | 8 |
| 1 | $CH_2$ | $NH_2$ | H | H | H | H | H | H | H | H |
| 2 | " | $NHCH_2CH_3$ | " | " | " | " | " | " | " | " |
| 3 | " | $NHCH(CH_3)_2$ | " | " | p-Cl | " | " | " | " | " |
| 4 | " | N-morpholine | " | " | o-$OCH_3$ | " | " | " | " | " |
| 5 | " | NH-(2-pyridine) | " | " | p-$OCH_3$ | o-$CH_3$ | o'-$CH_3$ | " | " | " |
| 6 | " | $NHOCH_3$ | " | " | H | H | H | " | " | " |
| 7 | " | $NHOCH_2Ph$ | " | $CH_3$ | " | " | " | $CH_3$ | $CH_3$ | " |
| 8 | " | $NHCH_2CH_3$ | " | H | p-$CF_3$ | " | " | H | H | 5-$NO_2$ |
| 9 | " | " | " | " | p-F | " | $CH_2CH_2CH_2$ | " | H |
| 10 | " | OH | " | " | p-$OCH_3$ | " | H | H | " | 5-F |
| 11 | " | " | " | " | o-$CH_3$ | " | " | CO | H |
| 12 | $C(CH_3)_2$ | $NH_2$ | " | $CH_3$ | p-Cl | " | " | H | H | 5-$OCH_3$ |
| 13 | " | " | " | H | H | " | $CH_2CH_2CH_2$ | " | 5-F |
| 14 | " | $N(CH_3)_2$ | " | " | p-$OCH_3$ | o-$OCH_3$ | H | CO | H |
| 15 | " | N-morpholine | " | " | o-$CF_3$ | H | " | H | H | 5-$OCH_3$ |
| 16 | " | OH | " | " | H | " | " | CO | 5-$NO_2$ |
| 17 | " | " | " | " | " | " | $CH_2CH_2CH_2$ | " | H | 5-Cl |
| 18 | $CH_2O(CH_2)_2$ | $N(CH_3)_2$ | " | " | o-$CF_3$ | " | H | H | " | H |
| 19 | " | OH | " | " | p-$NH_2COCH_3$ | " | " | " | " | 5-$OCH_3$ |
| 20 | $CH_2O(CH_2)_3$ | OH | " | " | H | " | " | CO | 5-F |
| 21 | " | $NH_2$ | " | " | m-$CH_3$ | " | " | " | H |
| 22 | $CH_2$ | " | " | " | H | " | " | H | H | 5-CN |
| 23 | " | " | " | " | " | " | " | " | " | 5-$CONH_2$ |

3921 Parr hydrogenator at room temperature, and stirred for 3 hours. The mixture was then filtered and the solution was evaporated under reduced pressure. The crude residue was dissolved in 1.5 N HCl (100 ml) and washed with diethyl ether (3×100 ml). The acidic phase was brought to basic pH with 10N NaOH and the solid thus formed was filtered off and purified by crystallization from benzene.

The product was dissolved in diethyl ether (100 ml) and treated at room temperature with an approximately 1N solution of HCl in diethyl ether.

The solid thus formed was filtered off and purified by crystallization from absolute ethanol.

10.0 g of 2-amino-1-(1-benzyl-1H-indazol-3-yl)ethanol were thus obtained.

m.p.=126° C. with decomposition $^1$H-NMR (DMSO-d6, δ ppm): 3.26 (d, J=6.87 Hz, 2H), 5.29 (q, J=5.90 Hz, 1H), 5.63 (s, 2H), 6.31 (d, J=5.12 Hz, 1H), 7.15 (t, J=7.45 Hz, 1H), 7.21-7.35 (m, 5H), 7.38 (t, J=7.67 Hz, 1H), 7.67 (d, J=8.62 Hz, 1H), 7.94 (d, J=8.04 Hz, 1H), 8.30 (bs, 2H).

Preparation of Compound 2

1-(1-benzyl-1H-indazol-3-yl)-2-(ethylamino)ethanol

A mixture of 1-(1-benzyl-1H-indazol-3-yl)-2-chloroethanol (8.8 g; 0.031 mol) and ethylamine (7 g; 0.155 mol) in benzene (60 ml) was heated at 130° C. in a closed tube for 8 hours. The reaction was completed by cooling the mixture to room temperature and washing with water (3×20 ml). The organic phase was then extracted with 1N HCl (3×50 ml). The combined acidic phases were washed with diethyl ether (3×50 ml) and then brought to basic pH with 25% NaOH solution. The precipitated solid was filtered off, dissolved in chloroform (200 ml) and washed with water until neutral. The solvent was then concentrated under reduced pressure and the crude residue was purified by crystallization from benzene.

The solid was then dissolved in isopropanol (150 ml) and treated at room temperature with an approximately 1N solution of HCl in diethyl ether. The precipitated product was filtered off and purified by crystallization from isopropanol. 4.8 g of 1-(1-benzyl-1H-indazol-3-yl)-2-(ethylamino)ethanol hydrochloride were obtained.

m.p.=153-154° C.

$^1$H-NMR (DMSO-d6, δ ppm): 1.25 (t, J=7.27 Hz, 3H), 3.05 (q, J=7.16 Hz, 2H), 3.29-3.43 (m, 2H), 5.36-5.49 (m, 1H), 5.63 (s, 2H), 6.39 (d, J=4.95 Hz, 1H), 7.16 (ddd, J=8.01; 7.02; 0.83 Hz, 1H), 7.21-7.35 (m, 5H), 7.39 (ddd, J=8.38; 6.98; 0.99 Hz, 1H), 7.68 (d, J=8.60 Hz, 1H), 7.96 (dt, J=8.13; 0.89 Hz, 1H), 8.65-9.63 (m, 1H).

Example 1

Analysis of the Gene Expression of MCP-1 in a Human Monocyte Line

The capacity of compound 1 to inhibit the expression of MCP-1 by lipopolysaccharide (LPS)-stimulated MonoMac6 cells was evaluated. The cells were placed in 96-well plates at a concentration of 50 000 cells/well. The compound was tested at the maximum soluble concentration given in Table 1 (in the range 30-300 μM) and incubated for 1 hour. The cells were then stimulated with LPS (100 ng/ml) for 4 hours.

The total RNA was extracted from the cell pellet using the RNeasy mini kit (Qiagen), reverse-transcribed with the TaqMan Reverse transcription reagents synthesis kit (Applied Biosystems) and the cDNA obtained was used for the real-time PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human MCP-1 was used (Applied Biosystems, RefSeq NM_002982.3). A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 1 below.

TABLE 1

| No. | % inhibition | [μM] |
|---|---|---|
| 1 | 64 | 150 |
| 2 | 53 | 150 |

As shown by the results obtained and given in Table 1, compound 1 and 2 were capable of significantly inhibiting the LPS-induced expression of MCP-1 in a human monocyte line, and showed a reduction in the levels of specific mRNA of 64% and 53%, respectively.

Example 2

Measurement of the Production of MCP-1 in a Human Monocyte Line

The capacity of the compounds 1 and 2 to inhibit the expression of the protein MCP-1 by lipopolysaccharide (LPS)-stimulated MonoMac6 cells was evaluated. The cells were placed in 96-well plates at a concentration of 50 000 cells/well. The compounds were tested at the maximum soluble concentration given in Table 2 (in the range 30-300 μM) and incubated for 1 hour. The cells were then stimulated with LPS (100 ng/ml) for 20 hours.

The amount of MCP-1 produced was measured in the supernatants, suitably diluted with buffer, by means of an immunoenzymatic test (ELISA) using a commercial kit (ELISA MCP-1/JE, R&D Systems).

The results obtained, expressed as a percentage of inhibition, are collated in Table 2 below.

TABLE 2

| No. | % inhibition | [μM] |
|---|---|---|
| 1 | 73 | 150 |
| 2 | 67 | 150 |

As shown by the results obtained and given in Table 2, the compounds 1 and 2 of the present invention were capable of significantly inhibiting the LPS-induced expression of MCP-1 in a human monocyte line, and showed a reduction in the levels of produced protein of 73% and 67%, respectively.

Example 3

Analysis of the Gene Expression of CX3CR1 in a Human Monocyte Line

The capacity of compound 1 to inhibit the expression of CX3CR1 by lipopolysaccharide (LPS)-stimulated Mono- Mac6 cells was evaluated. The cells were placed in 96-well plates at a concentration of 50 000 cells/well. The compound was tested at the maximum soluble concentration given in Table 3 (in the range 30-300 μM) and incubated for 1 hour. The cells were then stimulated with LPS (100 ng/ml) for 20 hours.

The total RNA was extracted from the cell pellet using the RNeasy mini kit (Qiagen), reverse-transcribed with the TaqMan Reverse transcription reagents synthesis kit (Applied Biosystems) and the cDNA obtained was used for the realtime PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human CX3CR1 was used (Applied Biosystems, RefSeq NM_001337.3). A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 3 below.

TABLE 3

| No. | % inhibition | [μM] |
|---|---|---|
| 1 | 96 | 150 |
| 2 | 85 | 150 |

As shown by the results obtained and given in Table 3, compound 1 and 2 of the present invention were capable of significantly inhibiting the LPS-induced expression of CX3CR1 in a human monocyte line, and showed a reduction in the levels of specific mRNA of 96% and 85%, respectively.

The invention claimed is:
1. A compound represented by formula (I):

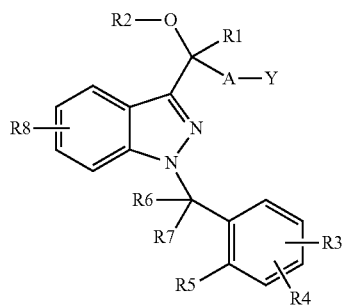

wherein:
A is —$X_1$— or —$X_1$—O—$X_2$—, in which
$X_1$ is an alkylene group having from 1 to 5 carbon atoms, optionally substituted with one or more alkyl groups having from 1 to 5 carbon atoms or one or more alkoxy groups having from 1 to 3 carbon atoms, and
$X_2$ is an alkylene group having from 1 to 5 carbon atoms, optionally substituted with one or more alkyl groups having from 1 to 5 carbon atoms,
Y is hydrogen, —OH, —N($R_{11}$)($R_{12}$), or —N($R_{11}$)O($R_{12}$), wherein
$R_{11}$ is hydrogen, an alkyl group having from 1 to 5 carbon atoms, or an alkoxy group having from 1 to 3 carbon atoms, or $R_{11}$ together with $R_{12}$ forms a 4- to 7-membered heterocycle,
$R_{12}$ is hydrogen, an alkyl group having from 1 to 5 carbon atoms, an alkoxy group having from 1 to 3 carbon atoms, an aryl group, a heteroaryl group, an alkylaryl group, an alkylheteroaryl group, —COR', —COOR', or —CON(R')(R''), wherein R' and R'', which may be identical or different from each other, are each independently hydrogen or an alkyl group having from 1 to 5 carbon atoms, or $R_{12}$ together with $R_{11}$, forms a 4- to 7-membered heterocycle,
$R_1$ and $R_2$, which may be identical or different from each other, are each independently hydrogen or an alkyl group having from 1 to 5 carbon atoms,
$R_3$, $R_4$ and $R_8$, which may be identical or different from each other, are each independently hydrogen, an alkyl group having from 1 to 5 carbon atoms, an alkoxy group having from 1 to 3 carbon atoms, a halogen atom, —OH, —N(R')(R''), —N(R')COR'', —CN, —CONR'R'', —$SO_2$NR'R'', —$SO_2$R', nitro or trifluoromethyl; wherein R' and R'', which may be identical or different from each other, are each independently hydrogen or an alkyl group having from 1 to 5 carbon atoms,
$R_5$ is hydrogen, an alkyl group having from 1 to 5 carbon atoms, an alkoxy group having from 1 to 3 carbon atoms, a halogen atom, —OH, —N(R')(R''), —N(R')COR'', nitro or trifluoromethyl, or $R_5$ together with one of either $R_6$ or $R_7$ forms a ring having 5 or 6 carbon atoms; wherein R' and R'', which may be identical or different from each other, are each independently hydrogen or an alkyl group having from 1 to 5 carbon atoms,
$R_6$ and $R_7$, which may be identical or different from each other, are each independently hydrogen or an alkyl group having from 1 to 5 carbon atoms, or $R_6$ and $R_7$ together form a group C=O, or one of either $R_6$ or $R_7$, together with $R_5$, forms a ring having 5 or 6 carbon atoms,
or a pharmaceutically acceptable salt thereof or a pharmaceutically acceptable ester thereof.

2. The compound, pharmaceutically acceptable salt, or pharmaceutically acceptable ester according to claim 1, wherein $X_1$ is an alkylene group having from 1 to 4 carbon atoms, optionally substituted with one or more alkyl groups having from 1 to 3 carbon atoms, and $X_2$ is an alkylene group having from 1 to 4 carbon atoms, optionally substituted with one or more alkyl groups having from 1 to 3 carbon atoms or one or more alkoxy groups having 1 or 2 carbon atoms.

3. The compound, pharmaceutically acceptable salt, or pharmaceutically acceptable ester according to claim 1, wherein $X_1$ is selected from the group consisting of —$CH_2$—, —$CH_2CH_2$—, —$C(CH_3)_2$—, and —$C(CH_3)_2CH_2$— and $X_2$ is selected from the group consisting of —$CH_2$—, —$CH_2CH_2$—, —$CH_2CH_2CH_2$—, —$C(CH_3)_2$—, —$C(CH_3)_2$ $CH_2$—, and —$CH_2C(CH_3)_2CH_2$—.

4. The compound, pharmaceutically acceptable salt, or pharmaceutically acceptable ester according to claim 1, wherein A is selected from the group consisting of —$CH_2$—, $C(CH_3)_2$—, —$CH_2OCH_2CH_2$—, and —$CH_2OCH_2CH_2CH_2$—.

5. The compound, pharmaceutically acceptable salt, or pharmaceutically acceptable ester according to claim 1, wherein $R_{11}$ and $R_{12}$, which may be identical or different from each other, are each independently a hydrogen atom or an alkyl group having from 1 to 3 carbon atoms, or $R_{11}$ and $R_{12}$ together form a 5- or 6-membered heterocycle.

6. A compound, pharmaceutically acceptable salt, or pharmaceutically acceptable ester according to claim 1, wherein $R_1$ and $R_2$, which may be identical or different from each other, are each independently a hydrogen atom or an alkyl group having from 1 to 3 carbon atoms.

7. The compound, pharmaceutically acceptable salt, or pharmaceutically acceptable ester according to claim 1, wherein $R_3$, $R_4$ and $R_8$, which may be identical or different from each other, are each independently a hydrogen atom, an alkyl group having from 1 to 3 carbon atoms, an alkoxy group having 1 or 2 carbon atoms, a Br atom, a Cl atom, a F atom, an OH group, a nitro group, a trifluoromethyl group, —N(R')(R"), —N(R')COR", —CN, —CONR'R", —SO$_2$NR'R", or —SO$_2$R', wherein R' and R", which may be identical or different from each other, are each independently a hydrogen atom or an alkyl group having from 1 to 3 carbon atoms.

8. The compound, pharmaceutically acceptable salt, or pharmaceutically acceptable ester according to claim 1, wherein $R_5$ is a hydrogen atom, an alkyl group having from 1 to 3 carbon atoms, an alkoxy group having 1 or 2 carbon atoms, a halogen atom, or an OH group, or $R_5$, together with one of either $R_6$ or $R_7$, forms a ring having 5 or 6 carbon atoms.

9. The compound, pharmaceutically acceptable salt, or pharmaceutically acceptable ester according to claim 1, wherein $R_6$ and $R_7$, which may be identical or different from each other, are each independently a hydrogen atom or an alkyl group having from 1 to 3 carbon atoms, or $R_6$ and $R_7$ together form a group C=O, or one of either $R_6$ or $R_7$, together with $R_5$, forms a ring having 5 or 6 carbon atoms.

10. A pharmaceutical composition, comprising a compound, pharmaceutically acceptable salt, or pharmaceutically acceptable ester according to claim 1 and at least one pharmaceutically acceptable vehicle.

11. The pharmaceutical composition according to claim 10, wherein said pharmaceutically acceptable salt is an addition salt with a physiologically acceptable acid or base.

12. The pharmaceutical composition according to claim 11, wherein said physiologically acceptable acid is selected from the group consisting of hydrochloric acid, hydrobromic acid, sulfuric acid, phosphoric acid, nitric acid, acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid, and tartaric acid.

13. The pharmaceutical composition according to claim 11, wherein said physiologically acceptable base is selected from the group consisting of ammonium hydroxide, calcium hydroxide, magnesium carbonate, sodium hydrogen carbonate, potassium hydrogen carbonate, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl) pyrrolidine, isopropylamine, lysine, methylglucamine, morpholine, piperazine, piperidine, theobromine, triethylamine, trimethylamine, tripropylamine, and tromethamine.

14. The pharmaceutical composition according to claim 10, wherein said pharmaceutically acceptable ester is formed with a physiologically acceptable organic acid selected from the group consisting of acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid, and tartaric acid.

15. The pharmaceutical composition according to claim 10, wherein said pharmaceutically acceptable vehicle is selected from the group consisting of a glidant, a binder, a disintegrant, a filler, a diluent, a flavoring, a colorant, a fluidizer, a lubricant, a preserving agent, a humectant, an absorbent, and a sweetener.

16. A compound, pharmaceutically acceptable salt, or pharmaceutically acceptable ester according to claim 1, wherein A is —$X_1$—O—$X_2$—.

17. A compound, pharmaceutically acceptable salt, or pharmaceutically acceptable ester according to claim 16, wherein $X_1$ is selected from the group consisting of —CH$_2$—, —CH$_2$CH$_2$—, —C(CH$_3$)$_2$—, and —C(CH$_3$)$_2$CH$_2$— and $X_2$ is selected from the group consisting of —CH$_2$—, —CH$_2$CH$_2$—, —CH$_2$CH$_2$CH$_2$—, —C(CH$_3$)$_2$—, —C(CH$_3$)$_2$CH$_2$—, and —CH$_2$C(CH$_3$)$_2$CH$_2$—.

18. A compound, pharmaceutically acceptable salt, or pharmaceutically acceptable ester according to claim 16, wherein A is selected from the group consisting of —CH$_2$OCH$_2$CH$_2$— and —CH$_2$OCH$_2$CH$_2$CH$_2$—.

19. A compound, pharmaceutically acceptable salt, or pharmaceutically acceptable ester according to claim 16, wherein $R_{11}$ and $R_{12}$, which may be identical or different from each other, are each independently a hydrogen atom or an alkyl group having from 1 to 3 carbon atoms, or $R_{11}$ and $R_{12}$ together form a 5- or 6-membered heterocycle.

20. A compound, pharmaceutically acceptable salt, or pharmaceutically acceptable ester according to claim 16, wherein $R_1$ and $R_2$, which may be identical or different from each other, are each independently a hydrogen atom or an alkyl group having from 1 to 3 carbon atoms.

21. A compound, pharmaceutically acceptable salt, or pharmaceutically acceptable ester according to claim 16, wherein $R_3$, $R_4$ and $R_8$, which may be identical or different from each other, are each independently a hydrogen atom, an alkyl group having from 1 to 3 carbon atoms, an alkoxy group having 1 or 2 carbon atoms, a Br atom, a Cl atom, a F atom, an OH group, a nitro group, a trifluoromethyl group, —N(R')(R"), —N(R')COR", —CN, —CONR'R", —SO$_2$NR'R", or —SO$_2$R', wherein R' and R", which may be identical or different from each other, are each independently a hydrogen atom or an alkyl group having from 1 to 3 carbon atoms.

22. A compound, pharmaceutically acceptable salt, or pharmaceutically acceptable ester according to claim 16, wherein $R_5$ is a hydrogen atom, an alkyl group having from 1 to 3 carbon atoms, an alkoxy group having 1 or 2 carbon atoms, a halogen atom, or an OH group, or $R_5$, together with one of either $R_6$ or $R_7$, forms a ring having 5 or 6 carbon atoms.

23. A compound, pharmaceutically acceptable salt, or pharmaceutically acceptable ester according to claim 16, wherein $R_6$ and $R_7$, which may be identical or different from each other, are each independently a hydrogen atom or an alkyl group having from 1 to 3 carbon atoms, or $R_6$ and $R_7$ together form a group C=O, or one of either $R_6$ or $R_7$, together with $R_5$, forms a ring having 5 or 6 carbon atoms.

24. A pharmaceutical composition, comprising a compound, pharmaceutically acceptable salt, or pharmaceutically acceptable ester according to claim 16 and at least one pharmaceutically acceptable vehicle.

* * * * *